United States Patent [19]

Batters

[11] Patent Number: 4,554,923
[45] Date of Patent: Nov. 26, 1985

[54] ELECTRICAL THERAPEUTIC ASSEMBLY AND METHOD FOR REDUCING PAIN AND EDEMA IN A HAND

[76] Inventor: Robert C. Batters, 3125 Boulder Way, Eastpoint, Ga. 30344

[21] Appl. No.: 413,103

[22] Filed: Aug. 30, 1982

[51] Int. Cl.[4] .......................... A61N 1/32; A61N 1/04
[52] U.S. Cl. ..................................... 128/421; 128/796
[58] Field of Search ................ 128/798, 800, 26, 796, 128/421–422

[56] References Cited

U.S. PATENT DOCUMENTS

| | | | |
|---|---|---|---|
| 1,498,059 | 6/1924 | Tyler | 128/798 |
| 1,545,413 | 7/1925 | Elmvall | 128/800 |
| 1,989,282 | 8/1933 | Kimble et al. | 128/798 |
| 4,147,171 | 4/1979 | Greene et al. | 128/421 |
| 4,207,904 | 6/1980 | Greene | 128/798 |
| 4,233,986 | 11/1980 | Tannenbaum | 128/421 |
| 4,240,437 | 12/1980 | Church | 128/798 |

FOREIGN PATENT DOCUMENTS

| | | | |
|---|---|---|---|
| 0060925 | 2/1892 | Fed. Rep. of Germany | 128/796 |
| 0371553 | 1/1907 | France | 128/798 |

Primary Examiner—Edward M. Coven
Assistant Examiner—Steven Falk
Attorney, Agent, or Firm—Neil F. Markva

[57] ABSTRACT

An electrical therapeutic assembly and method for reducing pain and edema in a hand uses an electrically conducting material contiguously disposed with respect to the skin on an area enveloped by said conducting material. The skin is free of any externally applied mediums so that there is a substantially dry contact between the skin and the electrically conducting medium. A substantially uniform electric current is passed throughout the entire conducting medium to apply the current to the enveloped area. The electric current is applied at a shock pulse rate sufficient to reduce pain in the enveloped area without causing heat build-up within the tissue of the human body. A particular feature of the assembly makes use of a woven, mesh metal material that is in direct contact with the area of the human body and effective to apply electrical shock pulses over the entire enveloped area. The metal mesh material is in the form of a glove for enveloping a hand.

14 Claims, 7 Drawing Figures

ELECTRICAL THERAPEUTIC ASSEMBLY AND METHOD FOR REDUCING PAIN AND EDEMA IN A HAND

FIELD OF THE INVENTION

This invention is related to the therapeutic treatment of the hand of the human body subjected to pain due to inflammation, trauma, or operative procedures. More particularly, the invention is directed to the treatment of painful areas of the human hand through the use of electrical shock pulses.

BACKGROUND OF THE INVENTION

The treatment of painful areas on the human body with electrical shock pulses is well known. The U.S. Pat. No. 1,583,087 discloses a known electrical therapeutic apparatus wherein a pad member is moistened and placed on any portion of the body and connected to an electrical circuit so that the patient will receive the desired electrical treatment. In this instance, the pad terminal comprises a metal plate and a particular type of mounting to accomodate an absorbent material used as a pad in combination with the metal plate.

The U.S. Pat. No. 3,055,372 discloses a device for the electrical treatment of body tissues which includes electrically conductive rubber electrodes for producing pulsations to muscles in the human body. Pairs of pads are required to apply such pulsations which are received through the use of a variable speed motor. This prior art device is used just to improve the tone and general health of the body parts. There is no disclosure of this device being able to reduce pain and edema in the human body.

The U.S. Pat. No. 4,014,345 discloses an electrode having a metal plate used in combination with a sponge which is used in a wet condition to apply low current electrical pulse signals to stimulate body nerves with the effect that pain and other circulatory difficulties might be relieved. This electrode has a retaining ring and a very specific interrelationship between the sponge, metal plate and retaining ring to achieve the results desired by the patentee in that instance.

The U.S. Pat. No. 3,817,252 discloses another type of electrode for transcutaneous stimulation with electrical impulses. In this prior art structure, the electrode incorporates the use of a wet sponge and is particularly made to be a disposable electrode. An interface pad is made of a foam material and is expressly used to prevent the direct contact between the skin and the electrically conducting diffusor screen. Again, this type of an electrode makes use of an externally applied liquid medium to establish an electrical connection across the surface of the area being treated.

None of the prior art electrodes used to apply electrical shock pulses to the human body are satisfactory to diminish pain in joints such as the knuckles of the hand. Particularly, people who have had operations as a result of fractures in the hand generally experience much pain. This occurs because one quarter of all the sensory nerves in the body are located in the hands. Consequently, they are extremely sensitive. An injury to a joint in the hand can produce such pain that the patient refuses to move the body part and can lead to a condition called "causalgic" hand.

A major disadvantage associated with prior art efforts as they are applied to edematous joints of the hands is: avoidance of a dependent position or placing the body part lower than the heart, which encourages still more edema. Thus, it is necessary to elevate the body part to treat edema which occurs as a result of pain.

When tissue is traumatized, fluid rushes to that area to swell the joint to limit motion so that the person will not cause further damage. The body provides its own splinting mechanism. For example, if a thumb is hit with a hammer, it immediately swells up so that the person cannot move their thumb and injure themselves more if a bone happened to be broken. Once edema has formed in the joint, its removal is a significant problem. The current treatment is to apply ice, compression and elevation (I.C.E.). This is the accepted first aid as administered with injuries involving soft tissue trauma. The chief concern is prevention of swelling so that an appropriate examination can be performed.

The prior art electrodes used to apply electrical shock pulses to the hand do not permit total conformity to the body part, and elevation of the injured area. Electrodes now being used to control pain and edema cover a smaller part of the involved area and offer a nonuniform impulse and associated discomfort when using higher voltages. The electrodes being used for applying electrical stimulation to the hand are either a two by two inch square plate with a sponge on it or a four by four inch type pad having a sponge conforming to a metal electrode. In both instances, the electrodes are either strapped or taped onto the hand to which the electrical stimulation is being applied. When a sponge is used it is in a wet condition in order to cause the current to be conducted to the surface of the skin. The prior art electrodes require the use of a gel or cream or some other type of lubricant so that there is no direct contact between the metal electrode itself and the surface of the skin. If the metal electrode were placed in direct contact with the skin, there would be an uncomfortable feeling of a prickly sensation or an uncomfortable electrical shock type of feeling. Known prior art electrodes are not capable of conforming to a joint such as a hand.

In most recent developments, it has been found that the best possible way to treat a limb or joint post operatively is to have constant motion at the joint. That is, such motion has been found to enhance circulation at the joint and thereby significantly speed up the healing process. Because the prior art electrodes have to be strapped on or taped in place in such a manner that they do not conform to the joint itself, such a desirable joint motion is significantly limited. Thus, the recommended treatment of traumatized joints through the effecting of movement is severely limited.

PURPOSE OF THE INVENTION

The primary object of the invention is to provide a method and an apparatus for effecting treatment of an injured hand without having to effect any external application of a liquid medium such as a salve, gel or water to establish a substantially uniform electric current over the area of the hand.

Another object of the invention is to provide a method and an apparatus for treating the highly sensitive area of the hand so that all of the joints of the hand may be treated simultaneously while the part is held in an elevated position for the reduction of pain and edema in the joints.

A further object of the invention is to provide a method and apparatus for treating joints in the hand which have been subjected to trauma or have been subjected to surgery for the purpose of relieving pain and edema therein without danger of heat buildup in the tissues of the body while maintaining a substantially uniform application of electrical shock pulses over the entire area of the hand enveloped by the apparatus of the invention.

Furthermore, the object of this invention is to provide an electrode which does not limit or impair range of motion from being performed actively or passively thereby allowing a further means of inhibiting joint pain, edema, and stiffness.

A further object of the invention is to overcome the disadvantages associated with the known types of electrodes and electrical nerve stimulators which are presently available for treatment with electrical shock pulses.

SUMMARY OF THE INVENTION

As disclosed and described herein, the method of the invention comprises the steps of enveloping the hand area of the body to be treated with an electrically conducting material contiguously disposed with respect to the skin of the hand. The skin may be free from any externally applied liquid medium so that there is a substantially dry contact between the skin and the electrically conducting material. The electrically conducting material is then electrically connected to a source of electric current and a substantially uniform electric current is passed throughout the entire conducting material to apply the current directly to the enveloped area. The electric current is applied at a shock pulse rate sufficient to reduce pain in the enveloped area without causing heat build-up within the tissue of the human body.

A particular feature of the invention with the use of a galvanic current is in applying the positively charged current to the electrode. This technique will drive the fluid within the area being treated away from the area of the pain. The electric current may be generated using a relatively high voltage of from about 200 to 525 volts while providing a microamperage current being applied at a pulse rate of from about 2 to 128 pulses per second. The pulse width is in the range of from about 150 to 350 microseconds.

The electrical therapeutic assembly of the invention comprises a glove composed of a woven, metal mesh material which is sufficiently flexible to envelope the hand area of the body in which there is pain. Electrically connecting means are used to connect the woven, metal mesh material to a source of electric current. The mesh material is effective to conduct a substantially uniform current over the entire area enveloped by the material to apply electric shock pulses directly to the enveloped area. The mesh material is further effective to produce the electrical shock pulses without causing heat build-up within the tissue of the human body and without the necessity of having an externally applied liquid medium on the skin of the enveloped area. Electrical connecting means include contact means fixed to the mesh material and clip contacts for electrically contacting the mesh material at any available location thereon. The latter type of connecting means may be effected after the mesh material has been placed around the area to be treated. This therefore makes the assembly an extremely versatile type of an electrode particularly in treatment of hands.

A further feature of the invention is to have a flexible, elastomeric material disposed around the mesh material to enhance the physical contact between the mesh material and the skin over the area of the human body to be treated. In one embodiment, the elastomeric material is integrally formed around the side of the mesh material that is not in direct contact with the skin.

A further feature of the invention is directed to the particular shape of the mesh material to fit the peculiarities of the various joints. Thus, the mesh material may be in the form of a glove when treating a hand, the form of a sock for treating the foot and ankle, the form of a sheet or blanket when treating large areas such as the back and in the shape of a sleeve which might be slipped over an elbow or knee. A fine wire mesh in the form of a wire cloth is useful in treating phantom pain which may occur with a prosthesis.

BRIEF DESCRIPTION OF THE DRAWINGS

Other objects of this invention will appear in the following description and appended claims, reference being made to the accompanying drawings forming a part of the specification wherein like reference characters designate corresponding parts in the several views.

DETAILED DESCRIPTION

Figure 1:
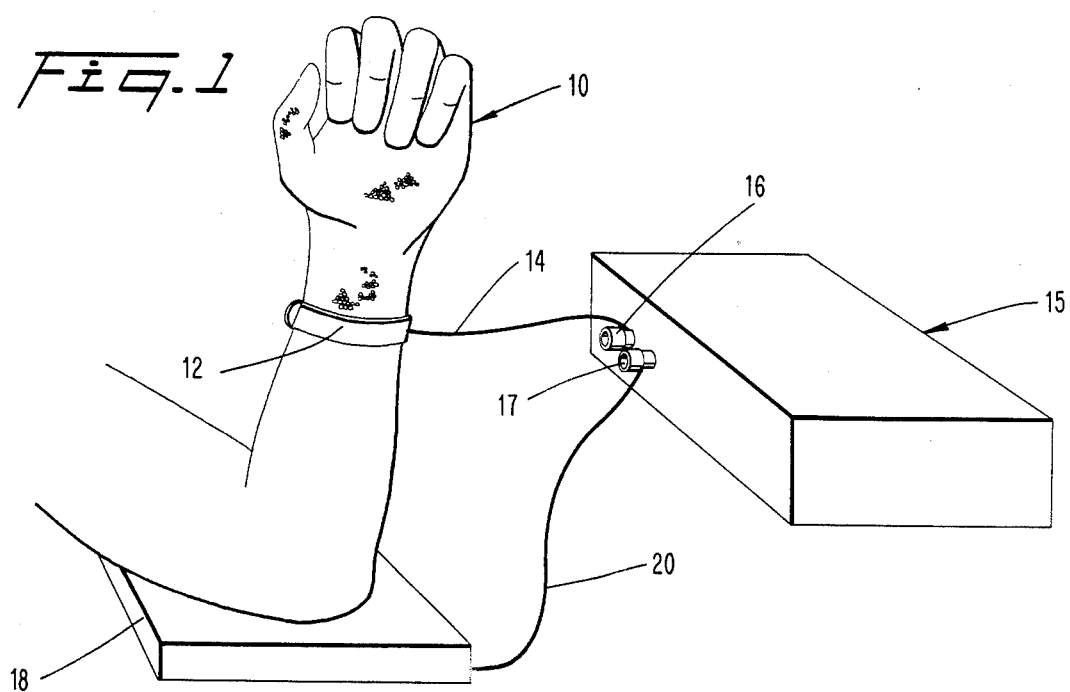
FIG. 1 is a perspective view showing the treatment of a hand with an electrode made in accordance with this invention.
Figure 2:
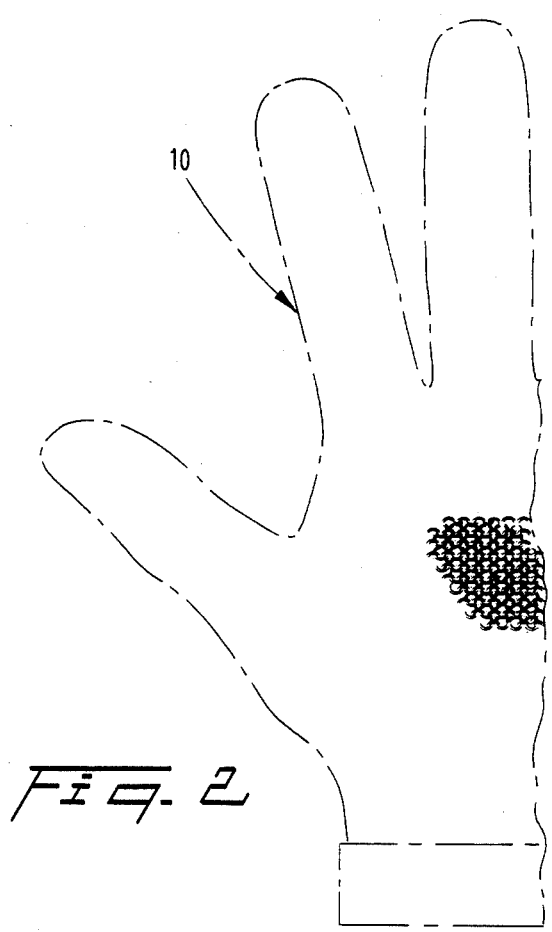
FIG. 2 is a fragmentary elevational view showing an electrode for a hand made in accordance with this invention.

The electrical therapeutic assembly as shown in FIG. 1 includes an electrically conducting material in the form of a glove 10 for enveloping the hand of a human body. Glove 10 is made of a woven, metal mesh material which is sufficiently flexible to envelope the entire hand and completely surround all the joints. The fine metal mesh glove 10 is composed of a series of loops as clearly shown in FIG. 2. The metal may be stainless steel, brass or aluminum. Glove 10 may be a safety glove marketed under the trademark Niroflex or manufactured by Whiting & Davis Co. of Plainsville, Mass. A strap 12 is disposed at the wrist and includes a Velcro fastening mechanism for holding glove 10 in place on the patient's hand. Glove 10 acts as a first electrode operating in conjunction with the electrical pulse producing device 15.

During treatment, the patient places his elbow on a second electrode 18. The second electrode may be any other type of electrode which is already available in the prior art such as a metal pad as discussed above. It might also be another piece of woven, mesh material. A lead 20 connects electrode 18 to the device 15. Coupling members 16 and 17 may be composed of any type of standard electrical connecting device such as a jack for connecting the leads 14 and 20, respectively, to the electrical pulse producing device 15.

Stimulating device 15 may be composed of a portable pulsed galvanic stimulator which produces a pulse rate of current of from about 2 to about 128 pulses per second. The pulse width may be from about 150 to about 350 microseconds. The rate of electric current from device 15 is measured in microamperage at a voltage in the range of from about 200 to about 525 volts. Such a stimulator is readily available and manufactured by Staodynamics, Inc. Another high voltage medical electronic pulser made by Dynawave Corporation of Geneva, Illinois produces high voltage unidirectional, short duration, twin-peaked pulses. The twin pulse repetition rate is selected of from 1 to 105 cycles per second. The pulse amplitude is voltage controlled and adjustable from 0 to 500 volts maximum with 500 microamps being a maximum current flow.

In a system of the type shown in FIG. 1, device 15 produces short duration pulses of electric current which are applied directly through an active electrode, which in the case of this invention, is the metal glove 10. The dispersive or inactive electrode 18 is connected to any convenient portion of the body that has enough mass and area to carry the current without excessive stimulation of this particular portion.

According to the prior art, bare metal against the skin does not ordinarily make a low resistance connection which is required in this type of therapy. Consequently, in the prior art methods, to assure low resistance, it is necessary to moisten the skin at the point at which the active electrode is to be placed. With the prior art methodology, the active electrode must be moved from point to point during treatment of the patient. Consequently, the applicator associated with the electrode must carry a considerable amount of moisture to make sure that there is a wet contact between the electrode and the skin. One of the problems of this prior art method is that the sponge used to hold the moisture may contract when it is dry and split if the threads are allowed to dry on the electrode.

However, with the use of a woven, metal mesh material such as found in the glove 10, it is no longer necessary to use a moisture containing material such as a sponge for having a wet contact. That is, the skin on the hand is free from any externally applied medium so that there is a substantially dry contact between the skin and the electrically conducting material. This clearly overcomes several problems associated with the prior art methods as discussed above. Once the glove 10 is electrically connected to the stimulating device 15, a substantially uniform electric current is passed throughout the entire conducting material along the various strands of the mesh to apply the current to the enveloped area of the body. In this instance, glove 10 envelops the entire hand and all of its joints. The current is applied at a shock pulse rate sufficient to reduce pain in the enveloped area without causing heat build-up within the tissue of the human body. In a specific embodiment, the pulse rate of current has been used at about 8 pulses per second. The voltage of the device 15 is set at about 500 volts with an extremely low rate of current flow measured in microamps.

When glove 10 is a positive electrode, it is effective to reduce edema within the enveloped area of the body. That is, the fluid in the body has a positive charge. Thus, when the electrode has a positive charge it will repel the fluid in the body and cause it to move away from the swollen joints. On the other hand, if glove 10 constitutes a negative electrode it is effective to soften tissue within the enveloped area of the body.

The woven, mesh glove 10 enables the patient to hold his hand elevated as shown in FIG. 1. At the same time, with the use of the novel electrode 10, the patient is able to flex and move the joints of his hand during treatment in the elevated position. This result has never before been achievable using the electrodes of the prior art. The electrode glove 10 is totally conformable to the joints of the hand and the wire mesh is flexible enough that the active and passive range of motion can be carried out without any hinderence. Thus, circulation is enhanced and the healing process is greatly expedited.

Unlike prior art electrodes which are operating only in a local area on the body, the electrode glove 10 which conforms exactly to the joints of the hand, gives a uniform current to the joints instead of a localized current thereby preventing any build-up of current in a local area and a nonuniform application to the joint. The totally enveloped joint receives a uniform current and has a much more comfortable sensation. With the electrode glove 10, higher currents may be used without adversely affecting the body tissue that is enveloped. This is unlike the typical prior art electrodes where there is a build-up of current at one point thus significantly limiting the amount of current that may be used.

It is possible to treat the patient with either alternating or direct current. However, using alternating current it is not possible to treat the swelling or edema in the fashion described with the galvanic or direct current application. When using a pulse rate setting of 2 pulses per second, the pulse width is 350 microseconds. At 8 pulses per second, the pulse width is 250 microseconds and at 128 pulses per second, the pulse width is 150 microseconds.

The new and unexpected results flowing from the use of the woven, mesh glove 10 includes the overcoming of all the disadvantages associated with the prior art electrodes as discussed above. With such a woven, mesh material it has been found that, contrary to the prior art electrodes, no moisture or liquid is necessary to achieve the desired electrical current pulses which envelope the entire joint. In contrast, the prior art electrodes must necessarily be inclusive of a moisture producing pad or sponge material. The results of reduction of pain and swelling have been significant. Furthermore, the patient may be able to perform treatments on his own without supervision from a doctor or therapist. This is an extremely significant development in the treatment of pain and swelling for patients because such treatment is now available on a broad basis in the patient's home rather than by skilled therapists at a location other than their home.

A further new and unexpected result flowing from the use of a woven, mesh material as a dry contact electrode enables the instantaneous treatment of trauma patients such as in accidents attended to by emergency units and injuries suffered during athletic events. With the discovery of the electrode of this invention, it is now possible to provide instantaneous treatment directly at the site of the accident or injury. With such trauma, swelling is a problem that needs to be addressed immediately. With the electrode of the present invention, it is possible to use a high voltage in combination with a microamperage, galvanic current so that both pain and swelling can be treated immediately. The available transcutaneous electrical nerve stimulators (TENS units) which are already known for treating pain may be used to produce the stimulation through the woven, mesh electrode of the present invention. This will produce a much more uniform and effective stimulation for reducing pain.

The electrical connection may be fixed to the mesh material or may involve the use of clip contacts for electrically contacting the mesh material at any available location.

A copper wire twisted into the woven mesh may be used to electrically connect the woven, mesh glove 10 to the stimulator 15.

With the woven, mesh glove 10, the patient need not immerse his hand in water such as has been the practice with prior art electrodes when treating the hand.

Different size wire meshes may be used depending upon the particular application. In some applications of the invention, the wire mesh may be a cloth having from about 150 to about 500 wire strands per inch and the diameter of the wire strands being from about 0.0014 to about 0.0026 inch.

While the electrical therapeutic assembly and method for reducing pain and edema in a hand has been shown and described in detail, it is obvious that this invention is not to be considered as being limited to the exact form disclosed, and that changes in detail and construction may be made therein within the scope of the invention, without departing from the spirit thereof.

Having thus set forth and disclosed the nature of this invention, what is claimed is:

1. A method of reducing pain in the hand of a human body, said method comprising the steps of:
   (a) enveloping the hand of the body to be treated with a glove composed of an electrically conducting, woven, metal mesh material contiguously disposed with respect to the skin of the hand,
   (b) said skin being free from any externally applied medium so that there is a substantially dry contact between the skin and the electrically conducting material,
   (c) electrically connecting the electrically conducting mesh material to a source of electric current,
   (d) passing a substantially uniform electric current throughout the entire conducting material to apply said current to said hand,
   (e) applying said current at a shock pulse rate sufficient to reduce pain in said enveloped hand without causing heat buildup within the tissue of the hand area.

2. A method as defined in claim 1, wherein the pulse rate of current is from about 2 to about 128 pulses per second.

3. A method as defined in claim 2, wherein the pulse rate of current is at about 8 pulses per second.

4. A method as defined in claim 1, wherein the pulse width is in the range of from about 150 to about 350 microseconds.

5. A method as defined in claim 1, wherein the rate of electric current is measured in microamperage at a voltage in the range of about 200 to about 525 volts.

6. A method as defined in claim 1, wherein the electric current is galvanic current.

7. A method as defined in claim 6, wherein the electrically conducting material constitutes a positive electrode and is effective to reduce edema within the enveloped hand area.

8. A method as defined in claim 6, wherein the electrically conducting material constitutes a negative electrode and is effective to soften tissue within the enveloped hand area.

9. A method as defined in claim 1, wherein said metal material comprises a woven, mesh cloth having from about 150 to about 500 wire strands per inch and the diameter of the wire strands is from about 0.0014 to about 0.0026 inch.

10. An electrical therapuetic assembly for reducing pain and edema in the hand of a human body, said assembly comprising:
    (a) mesh means for enveloping the hand of a human body for conducting a substantially uniform current over the entire area of the hand enveloped by the mesh means for applying electrical shock pulses directly to said enveloped area without the necessity of having an externally applied liquid medium on the skin of the enveloped hand area and without causing heat buildup within the tissue of the hand area,
    (b) said mesh means comprising a woven, metal mesh material which is sufficiently flexible and shaped as a glove to envelope the hand or parts thereof in which there is pain, and
    (c) means for electrically connecting the woven, mesh metal material to a source of electric current.

11. An assembly as defined in claim 10, wherein the electrically connecting means includes contact means fixed to the mesh material for effecting electrical contacts thereto.

12. An assembly as defined in claim 10, wherein the electrical connecting means includes clip contacts for electrically contacting the mesh material at any available location.

13. An assembly as defined in claim 10, wherein said metal material comprises a woven, mesh cloth having from about 150 to about 500 wire strands per inch and the diameter of the wire strands is from about 0.0014 to about 0.0026 inch.

14. A method of reducing pain in the hand of a human body, said method comprising the steps of:
    (a) enveloping the hand of the body to be treated with a glove having a mesh configuration and an electrically conducting metal material woven throughout the mesh configuration of the glove which is contiguously disposed with respect to the skin of the hand,
    (b) electrically connecting the electrically conducting metal material to a source of electric current,
    (c) passing a substantially uniform electric current throughout the entire conducting material to apply said current to the hand enveloped by the glove,
    (d) applying said current at a shock pulse rate sufficient to reduce pain in said enveloped hand without causing heat buildup within the tissue of the hand.

* * * * *